United States Patent
Shinohara et al.

(10) Patent No.: US 10,030,789 B2
(45) Date of Patent: Jul. 24, 2018

(54) DIAPHRAGM VALVE

(71) Applicant: FUJIKIN INCORPORATED, Osaka-shi (JP)

(72) Inventors: Tsutomu Shinohara, Osaka (JP); Michio Yamaji, Osaka (JP); Kouji Nishino, Osaka (JP); Ryousuke Dohi, Osaka (JP); Nobukazu Ikeda, Osaka (JP); Toshio Doh, Osaka (JP)

(73) Assignee: FUJIKIN INCORPORATED, Osaka-shi (JP)

( * ) Notice: Subject to any disclaimer, the term of this patent is extended or adjusted under 35 U.S.C. 154(b) by 73 days.

(21) Appl. No.: 14/896,113

(22) PCT Filed: May 12, 2014

(86) PCT No.: PCT/JP2014/062570
§ 371 (c)(1),
(2) Date: Dec. 4, 2015

(87) PCT Pub. No.: WO2014/196313
PCT Pub. Date: Dec. 11, 2014

(65) Prior Publication Data
US 2016/0123497 A1  May 5, 2016

(30) Foreign Application Priority Data

Jun. 4, 2013 (JP) .................................. 2013-118008

(51) Int. Cl.
*F16K 37/00* (2006.01)
*F16K 7/17* (2006.01)
*G01N 27/20* (2006.01)

(52) U.S. Cl.
CPC ............ *F16K 37/0083* (2013.01); *F16K 7/17* (2013.01); *G01N 27/20* (2013.01); *Y10T 137/5994* (2015.04)

(58) Field of Classification Search
CPC ........... F16K 37/00; F16K 7/17; G01N 27/20; Y10T 137/5994; G01L 19/0672; F04B 43/09
See application file for complete search history.

(56) References Cited

U.S. PATENT DOCUMENTS 3,131,638 A * 5/1964 Wilson .................. F04B 43/009
417/388
4,569,634 A * 2/1986 Mantell ............... G01L 19/0672
340/605
(Continued)

FOREIGN PATENT DOCUMENTS

JP          51-98463 A    8/1976
JP          58-109779 A   6/1983
(Continued)

OTHER PUBLICATIONS

International Search Report dated Jul. 8, 2014, issued for PCT/JP2014/062570.

Primary Examiner — Craig Schneider
Assistant Examiner — Kevin Barss
(74) Attorney, Agent, or Firm — Locke Lord LLP

(57) ABSTRACT

There is provided a diaphragm valve capable of reliably detecting damage to a diaphragm before breakage of the diaphragm in spite of the simple structure. A diaphragm includes a plurality of diaphragm layers. The uppermost diaphragm layer is provided with wiring. An abnormality of the diaphragm is detected by detecting breakage of the wiring.

6 Claims, 3 Drawing Sheets

(56) References Cited

U.S. PATENT DOCUMENTS

| | | | |
|---|---|---|---|
| 4,781,535 A | 11/1988 | Frawley et al. | |
| 5,163,327 A * | 11/1992 | Papai | G01L 19/12 73/715 |
| 5,581,019 A * | 12/1996 | Minor | C08J 9/32 285/910 |
| 5,820,105 A | 10/1998 | Yamaji et al. | |
| 5,851,004 A * | 12/1998 | Wu | F16K 7/14 251/331 |
| 6,935,180 B2 * | 8/2005 | Weisbrodt | F04B 43/0054 73/715 |
| 7,193,536 B2 * | 3/2007 | Shipman | G06F 3/0202 341/31 |
| 7,270,890 B2 * | 9/2007 | Sabol | C23C 4/18 416/61 |
| 7,467,582 B2 * | 12/2008 | Hembree | F04B 43/0054 92/103 R |
| 7,887,163 B2 * | 2/2011 | Tsukamoto | B41J 2/161 347/68 |
| 7,905,172 B2 * | 3/2011 | Ohrle | F04B 43/0054 417/395 |
| 8,144,918 B2 * | 3/2012 | Ikeda | H04R 7/045 381/152 |
| 2008/0202606 A1 | 8/2008 | O'Hara et al. | |

FOREIGN PATENT DOCUMENTS

| | | |
|---|---|---|
| JP | 1-142284 A | 6/1989 |
| JP | 2-56979 U | 4/1990 |
| JP | 06-341571 A | 12/1994 |
| JP | 9-14471 A | 1/1997 |
| JP | 2001-295925 A | 10/2001 |
| JP | 2002-168176 A | 6/2002 |
| JP | 2010-519488 A | 6/2010 |
| WO | WO-2010/136183 A1 | 12/2010 |

* cited by examiner

DIAPHRAGM VALVE

TECHNICAL FIELD

The present invention relates to a diaphragm valve and, more particularly, to a diaphragm valve capable of detecting the damage state during use.

BACKGROUND ART

There is a well-known diaphragm valve that includes a body provided with a fluid inflow passage, a fluid outflow passage, and a concave portion opened upward, an annular seat disposed on the bottom of the concave portion of the body, and an elastically deformable diaphragm which opens and closes a fluid passage by being pressed against or separated from the seat.

When the diaphragm of the diaphragm valve is broken, fluid in the valve may leak externally. When toxic gas or corrosive gas is used as the fluid, the leakage poses a risk.

Generally, the durability count of the diaphragm is checked in advance, the count until breakage is set in consideration of variations, and the diaphragm is replaced when this count is reached to prevent the diaphragm from being broken. However, the diaphragm may be broken before this count is reached.

Accordingly, PTL 1 discloses the provision of a sensor for monitoring the wear state of a diaphragm.

CITATION LIST

Patent Literature

PTL 1: JP-A-2010-519488

SUMMARY OF INVENTION

Technical Problem

When the damage state of a diaphragm is detected, the initial damage state before breakage of the diaphragm is preferably detected. In PTL 1, the damage state can be checked early by monitoring wear.

The technique in PTL 1 sets appropriate signal parameters, compares their change amount with the baseline measurement value, and obtains the wear state of the diaphragm. However, in such a system structure, the wear monitoring system is complicated and data processing is difficult, thereby leading to an increase in cost. In addition, it is also difficult to determine the point of occurrence of damage.

An object of the invention is to provide a diaphragm valve capable of reliably detecting damage to a diaphragm before breakage of the diaphragm in spite of the simple structure.

Solution to Problem

A diaphragm valve according to the present invention includes a body provided with a fluid inflow passage, a fluid outflow passage, and a concave portion opened upward, an annular seat disposed on a bottom of the concave portion of the body, and a diaphragm which opens and closes a fluid passage by being pressed against or separated from the seat, the diaphragm being elastically deformable, in which the diaphragm includes a plurality of diaphragm layers, wiring is provided on at least one of the plurality of diaphragm layers, and an abnormality of the diaphragm is detected by detecting breakage of the wiring.

The outer peripheral edge of the diaphragm is fixed to the body to seal the opening of the concave portion opened upward provided in the body, the middle portion is elastically deformable (movable upward or downward) with respect to the outer peripheral edge, and the elastic deformation accompanying upward or downward movement of a valve shaft contributes to the opening and closing of the fluid passage. The diaphragm may be made of metal or synthetic resin.

"Plurality" may be any number equal to or more than two. "At least one of the plurality of diaphragm layers" means that the wiring may be provided on all diaphragm layers, but the wiring is preferably provided on only one layer. In a diaphragm having a laminated structure, one diaphragm layer receiving the largest stress is generally broken and, since this reduces the entire strength, the entire diaphragm is broken. In the state in which only one diaphragm layer is broken, fluid in the valve does not leak. That is, if damage to one diaphragm is detected, a risk accompanying breakage of the diaphragm can be prevented before leakage of the fluid.

Breakage of the wiring is detected to determine whether one diaphragm layer is broken. That is, it is sufficient to detect the passing of current, so continuously changing detection values do not need to be compared with the threshold to make determination, thereby simplifying the structure for detecting the damage state before breakage of the entire diaphragm. The breakage of the wiring can be detected by passing current periodically (for example, once a day) and checking whether continuity is present.

Preferably, the plurality of diaphragm layers are made of metal, an insulating layer is provided between the wiring and the diaphragm layers, and the wiring is covered with a protective layer.

When the diaphragm layers are made of metal, the insulating layer is required. Preferably, the insulating layer and the protective layer are made of synthetic resin with durability and flexibility. For example, glass epoxy resin or fluororesin (such as PTFE or PFA) is adequate for such synthetic resin.

The thickness of the one diaphragm layer on which the wiring is provided may be smaller than thicknesses of the other diaphragm layers.

In this structure, since the diaphragm layer on which the wiring is provided is first broken reliably, the time when only one diaphragm layer is broken can be detected reliably.

Advantageous Effects of Invention

The diaphragm valve according to the invention detects the state in which one diaphragm layer is broken and fluid leakage does not occur, so damage to the diaphragm can be detected before occurrence of leakage of fluid.

Figure 1:
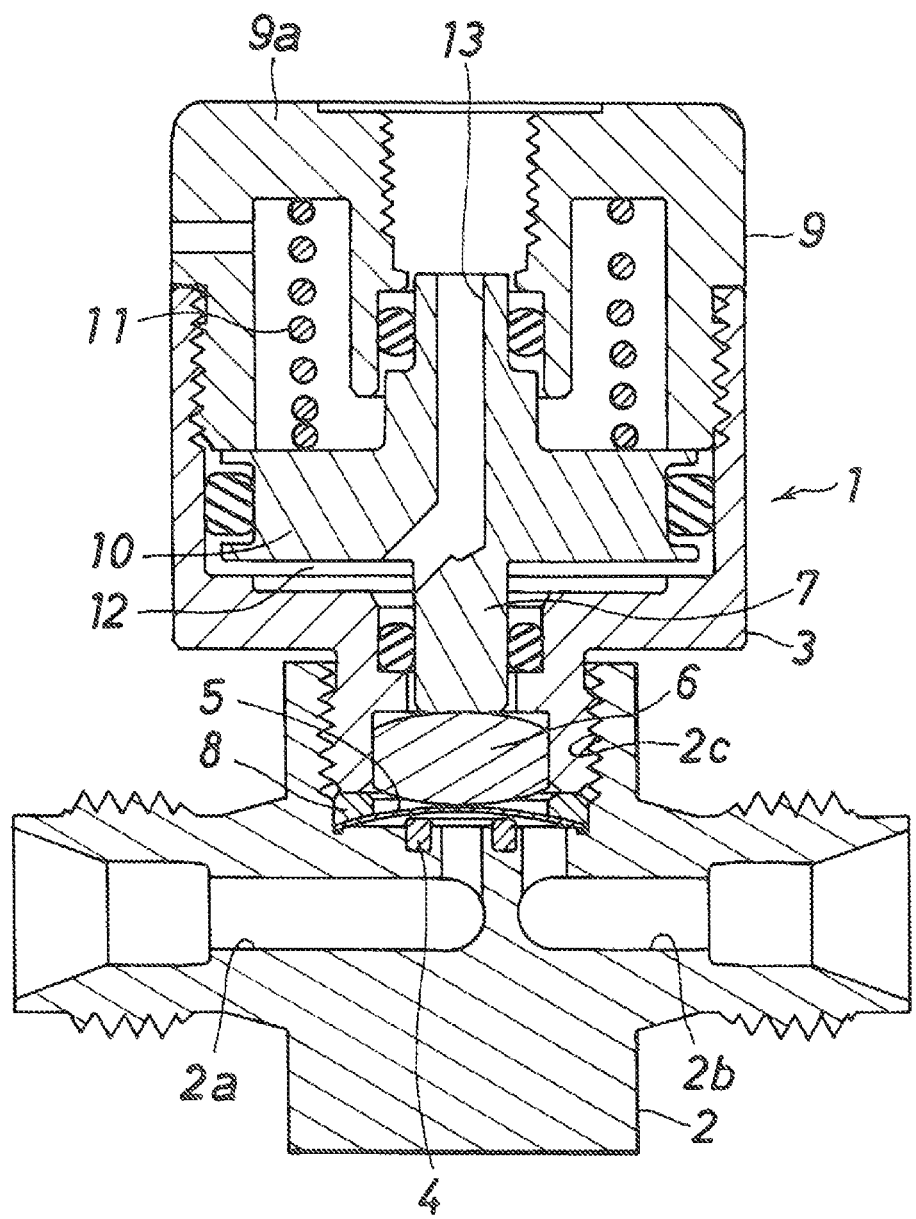
FIG. 1 is a cross sectional view illustrating a diaphragm valve according to an embodiment of the present invention.

REFERENCE SIGNS LIST (1): diaphragm valve
(2): body
(2a): fluid inflow passage
(2b): fluid outflow passage
(2c): concave portion
(5): diaphragm
(21), (22): diaphragm layer
(23): uppermost diaphragm layer
(24): wiring
(25): insulating layer
(26): protective layer

DESCRIPTION OF EMBODIMENTS

An embodiment of the present invention will be described below with reference to the drawings. Up and down in the following description indicate up and down in FIG. 1.

FIG. 1 illustrates a diaphragm valve according to an embodiment of the invention and a diaphragm valve (1) includes a block-shaped body (2) provided with a fluid inflow passage (2a), a fluid outflow passage (2b), and a concave portion (2c) opened upward, a cylindrical bonnet (3) extending upward, the cylindrical bonnet (3) having the lower end screwed with the upper part of the concave portion (2c) of the body (2), an annular seat (4) provided at the circumferential edge of the fluid inflow passage (2a), a diaphragm (5) which opens and closes the fluid inflow passage (2a) by being pressed against or separated from the seat (4), a diaphragm holder (6) holding the center of the diaphragm (5), a stem (7) inserted into the bonnet (3) so as to be movable upward and downward, the diaphragm (5) being pressed against or separated from the seat (4) by the stem (7) via the diaphragm holder (6), a holder adapter (8) disposed between the lower end surface of the bonnet (3) and a bottom of the concave portion (2c) of the body (2), the holder adapter (8) holding the outer peripheral edge of the diaphragm (5) between the holder adapter (8) and the bottom of the concave portion (2c) of the body (2), a casing (9) having a top wall (9a), the casing (9) being screwed with the bonnet (3), a piston (10) integrated with the stem (7), a compression coil spring (biasing member) (11) biasing the piston (10) downward, an operation air introduction chamber (12) provided on the lower surface of the piston (10), and an operation air introduction passage (13) introducing operation air to the operation air introduction chamber (12).

Figure 2:
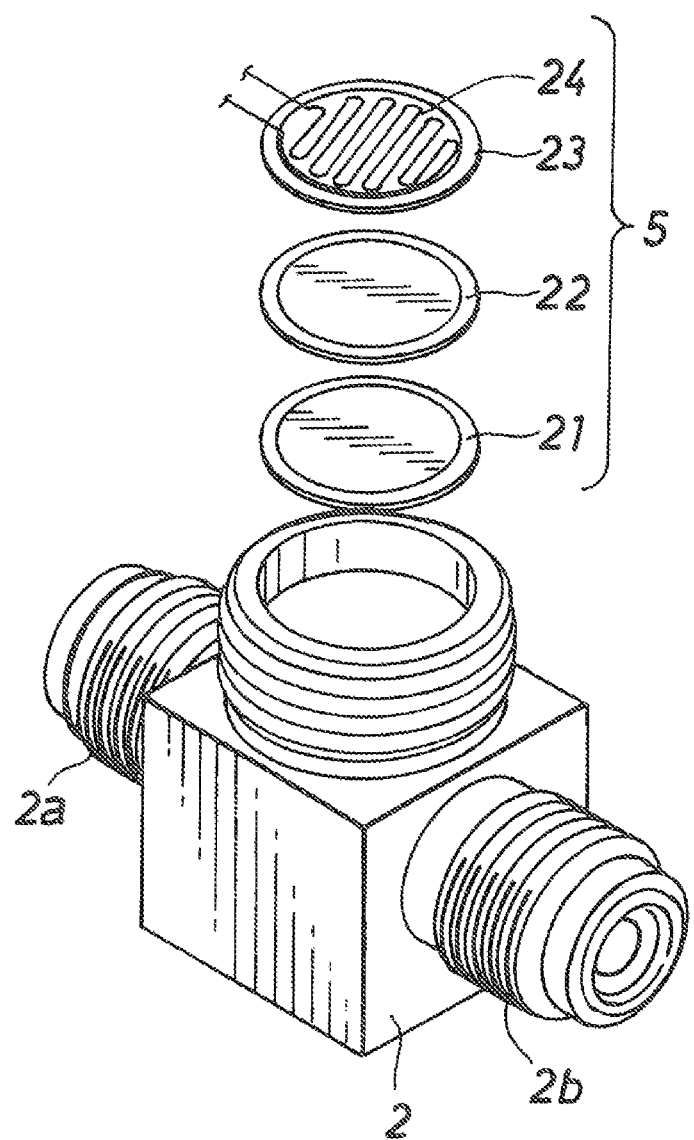
FIG. 2 is an exploded perspective view illustrating the structure of a diaphragm.

The diaphragm (5) is shaped like a spherical shell and projects upward in its natural state. The diaphragm (5) includes a plurality of (three in the diagram) diaphragm layers (21), (22), and (23), as illustrated in FIG. 2.

Figure 3:
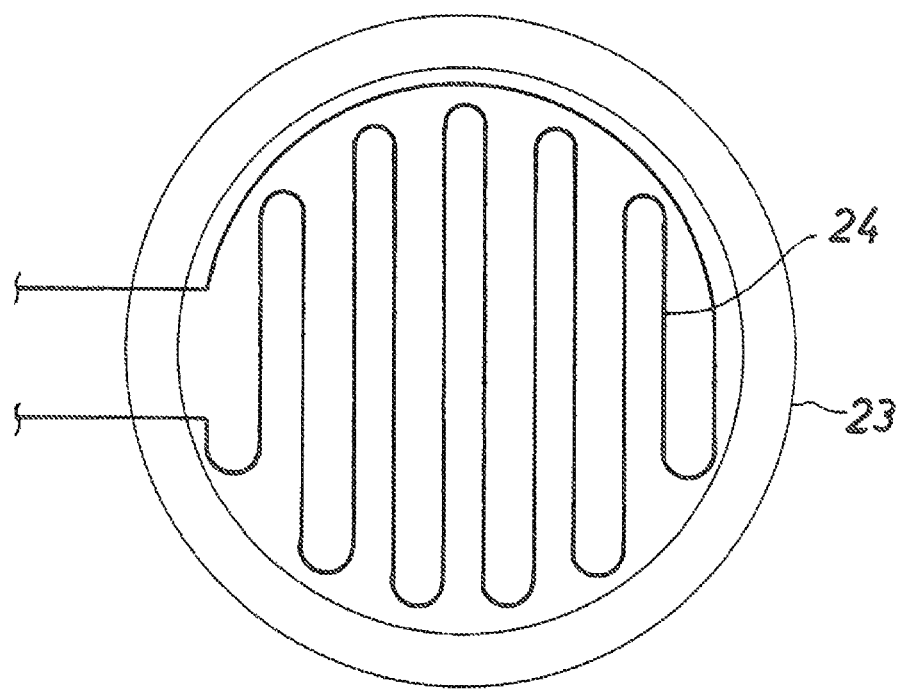
FIG. 3 is a plan view illustrating the uppermost diaphragm layer.

As illustrated in FIG. 3, wiring (24) is provided on the uppermost diaphragm layer (23) of the plurality of diaphragm layers (21), (22), and (23). The wiring (24) is connected to current pass detection means (not illustrated) detecting whether the pass state or the non-pass state is reached. Accordingly, when the wiring (24) of the uppermost diaphragm layer (23) is broken at one place, a shift from the pass state to the non-pass state occurs and the current pass detection means detects this change as the breakage of the uppermost diaphragm layer (23).

The uppermost diaphragm layer (23) is likely to be broken first since it receives the maximum stress among the plurality of diaphragm layers (21), (22), and (23). Accordingly, at the stage at which the uppermost diaphragm layer (23) is broken, the other diaphragm layers (21) and (22) are not broken. Therefore, fluid leakage, which becomes a problem when the entire diaphragm (5) is broken, does not occur. Since breakage of the uppermost diaphragm layer (23) can be detected only by checking whether current passes, the detection is simpler and more reliable than a detection system that, for example, has a sensor such as a strain gage installed in the diaphragm, obtains the amount of strain continuously, and detects presence or absence of damage by comparing the obtained amount with the threshold.

It is only necessary to supply current periodically (for example, once a day) and check whether current passes to detect breakage of the wiring (24). When current does not pass, the uppermost diaphragm layer (23) is determined to be broken and a necessity to replace the diaphragm (5) is transmitted externally via an LED and an IC tag.

The above diaphragm layers (21), (22), and (23) are formed by, for example, thin plates made of nickel alloy, which are cut out like circles and formed like spherical shells projecting their centers upward. The diaphragm layers (21), (22), and (23) may be formed by thin plates made of stainless steel or may be made of synthetic resin. All of the diaphragm layers (21), (22), and (23) do not need to be made of the same material and may be formed by alternately laminating, for example, a thin plate of stainless steel with a thin plate of nickel-cobalt alloy.

Figure 4:
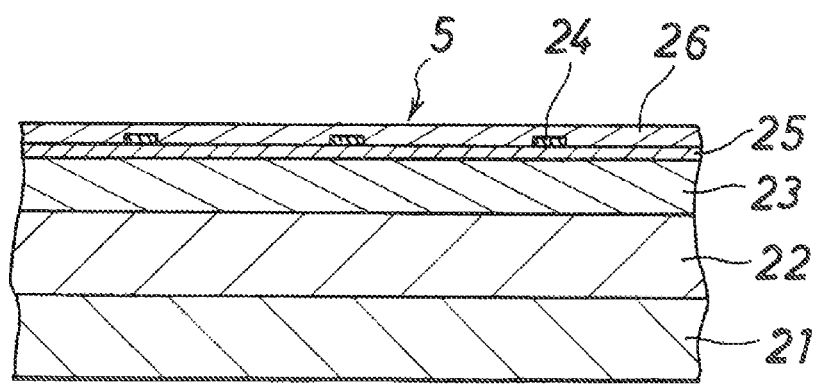
FIG. 4 is a cross sectional view schematically illustrating the structure of diaphragm layers according to the embodiment.

FIG. 4 illustrates a preferred embodiment when the diaphragm layers (21), (22), and (23) are made of metal. In this drawing, the wiring (24) is provided above the uppermost diaphragm layer (23), an insulating layer (25) is provided between the wiring (24) and the upper surface of the diaphragm layer (23), and the wiring (24) is covered with a protective layer (26).

More specifically, for example, a glass epoxy resin layer as the insulating layer (25) is provided on the upper surface of the uppermost diaphragm layer (23), the wiring (24) is provided thereon, and a PTFE (polytetrafluoroethylene) layer as the protective layer (26) is provided on the wiring (24) and the upper surface of the insulating layer (25) so as to cover the wiring (24). Fluororesin such as PTFE may be used in place of the glass epoxy resin layer and PFA (polyfluoroalkoxypolytetrafluoroethylene) or the like is used as fluororesin in addition to PTFE.

Although the diaphragm layers (21), (22), and (23) may have the same thickness in FIG. 4, the uppermost diaphragm layer (23) has a thickness smaller than those of the other diaphragm layers (21) and (22) in this embodiment.

Since the diaphragm layer (23) having the wiring (24) is provided with the insulating layer (25), the wiring (24), and the protective layer (26), the entire thickness including these layers becomes larger. This reinforces the diaphragm layer (23), so the diaphragm layers (21) and (22) may be broken earlier than the diaphragm layer (23) having the wiring (24) that should be broken first. As illustrated in FIG. 4, by reducing the thickness of the diaphragm layer (23) having the wiring (24), breakage of the diaphragm layer (23) that should be broken first can be detected reliably.

Since the diaphragm (5) is configured to include the three diaphragm layers (21), (22), and (23) in the above diaphragm valve (1), the necessary sealing performance is still ensured at the stage at which the uppermost diaphragm layer (23) is broken. Accordingly, replacement with a new diaphragm can be performed without a risk by detecting the breakage state of the uppermost diaphragm layer (23). For example, in the case of a semiconductor manufacturing apparatus, there is a possibility of damaging semiconductor products, but this structure prevents the semiconductor products from being damaged.

When all of the diaphragm layers (21), (22), and (23) are provided with wiring, the state in which one layer is broken can be detected more reliably. However, since the stress on the uppermost diaphragm layer (23) is generally maximum in the diaphragm (5) of laminate type and the uppermost diaphragm layer (23) is first broken, the structure becomes simpler by providing the wiring (24) on only the uppermost diaphragm layer (23).

Although the diaphragm (5) includes the three diaphragm layers (21), (22), and (23) in the above example, the diaphragm (5) may include two layers or four or more layers instead of the three diaphragm layers (21), (22), and (23).

In addition, the diaphragm (5) is shaped like a spherical shell above, but it may be shaped like a flat plate. The diaphragm may be used similarly in a structure in which the diaphragm does not directly make contact with the annular seat in addition to the structure in which the diaphragm is directly pressed against or separated from the seat.

Breakage of the wiring can be detected by passing current periodically and checking the continuity. In addition, damage to the diaphragm can be detected immediately by passing current constantly.

INDUSTRIAL APPLICABILITY

In a diaphragm valve, when a diaphragm is broken, fluid in the diaphragm valve may leak externally. However, since the damage state can be detected before the diaphragm is broken in the invention, even when toxic gas or corrosive gas is used as the fluid, a risk accompanying breakage of the diaphragm can be prevented. Accordingly, it is possible to contribute to the improvement of the safety of the diaphragm valve.

The invention claimed is:

1. A diaphragm valve comprising:
   a body provided with a fluid inflow passage, a fluid outflow passage, and a concave portion opened upward;
   an annular seat disposed on a bottom of the concave portion of the body; and
   a diaphragm which opens and closes a fluid passage by being pressed against or separated from the seat, the diaphragm being elastically deformable,
   wherein the diaphragm includes a first metal diaphragm layer and a second metal diaphragm layer separatable from each other forming a plurality of diaphragms, wiring is provided on only one of the plurality of metal diaphragm layers that receives the largest stress, an insulating layer is provided between the wiring and the diaphragm layer that received the largest stress and an abnormality of the diaphragm is detected by detecting breakage of the wiring.

2. The diaphragm valve according to claim 1, wherein the plurality of diaphragms further include a third metal diaphragm layer.

3. The diaphragm valve according to claim 1, wherein the wiring is covered with a protecting layer.

4. A diaphragm valve comprising:
   a body provided with a fluid inflow passage, a fluid outflow passage, and a concave portion opened upward;
   an annular seat disposed on a bottom of the concave portion of the body; and
   a diaphragm which opens and closes a fluid passage by being pressed against or separated from the seat, the diaphragm being elastically deformable,
   wherein the diaphragm includes a first metal diaphragm layer and a second metal plurality of diaphragm layer separatable from each other forming a plurality of diaphragms, wiring is provided on only the uppermost diaphragm layer of the plurality of metal diaphragm layers, an insulating layer is provided between the wiring and the uppermost diaphragm layer and an abnormality of the diaphragm is detected by detecting breakage of the wiring.

5. The diaphragm valve according to claim 4, wherein the plurality of diaphragms further include a third metal diaphragm layer.

6. The diaphragm valve according to claim 4 wherein the wiring is covered with a protective layer.

* * * * *